United States Patent [19]

McCoy

[11] 3,948,953

[45] Apr. 6, 1976

[54] DIOXOLANE DERIVATIVES HAVING SURFACTANT PROPERTIES

[75] Inventor: David R. McCoy, Wappingers Falls, N.Y.

[73] Assignee: Texaco Inc., New York, N.Y.

[22] Filed: Aug. 5, 1969

[21] Appl. No.: 847,729

[52] U.S. Cl. ............. 260/340.9; 252/351; 252/353; 252/550
[51] Int. Cl.² ............................................. C07D 317/24
[58] Field of Search ................................. 260/340.9

[56] References Cited
UNITED STATES PATENTS

| | | | |
|---|---|---|---|
| 2,789,124 | 4/1957 | Gilbert et al................ | 260/340.9 X |
| 3,206,474 | 9/1965 | Hechenbleikner et al... | 260/340.9 X |
| 3,246,012 | 4/1965 | Feit................................. | 260/340.9 |
| 3,264,322 | 8/1966 | Bertin............................. | 260/340.9 |

*Primary Examiner*—Richard J. Gallagher
*Assistant Examiner*—James H. Turnipseed
*Attorney, Agent, or Firm*—T. H. Whaley; C. G. Ries

[57] ABSTRACT

This invention concerns water soluble surfactants prepared by introducing solubilizing groups such as sulfates and polyoxyalkylenes into the dioxolane condensates of aliphatic ketones with glycerol.

11 Claims, No Drawings

DIOXOLANE DERIVATIVES HAVING SURFACTANT PROPERTIES

This invention concerns water solubilized ketals, their preparation and their utilization.

More particularly this invention relates to the solubilized condensates of glycerol with aliphatic ketones. These products are useful as surfactants, as components of detergent compositions and as organic intermediates, particularly pharmaceutical intermediates.

While all of the above condensates have utility as surfactants and/or as intermediates for organic transformations, as in any large class of compounds, there are frequently considerations which cause one or more substances falling within the scope of the broad class to be favored over the others. In this instance, dioxolane condensates of glycerol with aliphatic ketones containing 6 to 30 carbon atoms, wherein the solubilizing groups are selected from the group consisting of phosphate, alkoxylate and sulfate are favored because they are formed from relatively inexpensive reactants and exhibit substantially better surfactant properties than do the members of the broad class of condensates as a whole.

Within the above-designated group of dioxolane derivatives are the preferred dioxolane derivatives of this invention. These compounds are solubilized derivatives of 2,2-dialkyl-1,3-dioxolane-4-methylols having the structure:

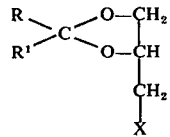

of which R and R' are the aliphatic residuum of the aliphatic ketone of the formula

wherein R and R', which can be the same or different alkyl groups, contain a total of 6 to 30 carbon atoms and X represents the solubilizing group preferably ethoxylate, sulfate or phosphate.

The terms "surfactant" or "surface-active," which are used throughout this disclosure, are synonymous and refer to substances which, in solution, are used by themselves or in conjunction with cleaning adjuvants such as additives or builders to form cleaning compositions. Solutions of surfactants are widely used to wet surfaces, remove soil, penetrate porous materials, disperse particles, emulsify oils and greases, etc., dependent upon the particular characteristics of the surfactant or surfactants used.

Desirably surfactants are stable, inexpensive, light colored materials which function at low concentration levels in solution and which can be produced from readily available starting materials, free from deleterious contaminants, preferably as easily handled, free-flowing liquids or powders.

Recently the applicants have found that the above described dioxolane derivatives not only satisfy all of these requirements but are produced in good yield in a form that easily and rapidly dissolve in aqueous solutions.

In its broadest contemplated process embodiment the surfactants of this invention are prepared by introducing at least one solubilizing group into the dioxolane reaction product formed by reacting glycerol with aliphatic ketones containing at least 6 carbon atoms in the molecule.

In its favored process embodiment at least one solubilizing group selected from the group consisting of phosphate, sulfate and polyoxyalkylate is introduced into a dioxolane prepared by condensing glycerol with aliphatic ketones containing between 6 to 30 atoms, until a water soluble surfactant is formed.

In its preferred process embodiment, a dioxolane prepared by condensing glycerol with a mixture of aliphatic ketones containing from about 10 to 15 carbon atoms is further treated with a source of solubilizing groups selected from the group consisting of chlorosulfonic acid, phosphoric acid, ethylene and propylene oxide, to produce a water-soluble surfactant.

In its most preferred process embodiment, a mixture of 2,2-dialkyl-4-hydroxymethyl-1,3-dioxolanes, derived from the acid-catalyzed condensation product of glycerol with a mixture of aliphatic ketones, (said ketones preferably derived from the dehydrogenation of secondary alcohols prepared by the boric acid-catalyzed air oxidation of linear hydrocarbons containing about 10 to 15 carbon atoms) is sulfated with a dialkyl ether-chlorosulfonic acid complex, until a sulfate grouping is introduced into said dioxolane, then treated with a basic substance such as ammonia gas, ammonium hydroxide and alkali metal basic salts until a water soluble surfactant is produced.

To further aid in the understanding of the inventive concept the following additional disclosure is submitted:

A. Aliphatic Ketones

The aliphatic ketones which are coreactants with glycerol to form the parent dioxolanes can be simple ketones or mixed ketones, containing from 6 to 30 carbon atoms. These ketones can be in the form of single highly purified compounds or in the form of mixtures of different ketones. The favored ketones are those containing from 10 to 15 carbon atoms, especially in the form of certain ketone mixtures derived from the dehydrogenation of secondary alcohols obtained from the boric acid-catalyzed air oxidation of linear hydrocarbons containing from about 10 to 15 carbon atoms. Illustrative simple ketones which can be used include di-n-propyl ketone, methyl butyl ketone, methyl pentyl ketone, dibutyl ketone, methyl nonyl ketone, dihexyl ketone, dioctyl ketone, dinonyl ketone, didecyl ketone, didodecyl ketone and the like.

B. Solubilizing Groups

In order to obtain good surfactant properties in the dioxolanes of this invention it is necessary to place at least one solubilizing group in the molecule. Solubilizing groups as used throughout this disclosure refers to groups which increase the solubility of the dioxolane in water to such an extent that the dioxolane exhibits surfactant properties. Illustrative solubilizing groups include sulfates (—OSO$_2$OH) chlorides, bromides, nitrates, phosphates, alkoxylates such as ethoxylate or propoxylate, and the water-soluble ammonium salts or alkali metal salts, where the solubilizing group permits their formation.

In most instances these solubilizing groups can be introduced into the dioxolane molecule by well known previously described techniques. For example, chlorides or bromides can be prepared using the appropriate phosphorus oxyhalides. Similarly the dioxolane can be alkoxylated between 50° and 175° to the extent where 1 to 20 or more groupings, preferably 4 to 14 groupings, are placed in the molecule using alkylene oxides such as ethylene, propylene or butylene oxides using strongly alkaline catalysts such as the alkali metals, i.e., sodium as well as their strongly alkali metal salts such as sodium and potassium hydroxides and alkoxides.

As indicated above, most of the water solublizing groups can be introduced into the dioxolane molecule using standard preparative techniques. However, in the case of the sulfate group ($-OSO_2OH$) quite unexpectedly prior art sulfation techniques either decomposed the dioxolane to the ketone or no reaction took place at all. For instance, oleum, sulfamic acid and chlorosulfonic acid alone and sulfur trioxide-pyridine complexes were unsuccessful in introducing the sulfate group into the molecule under a variety of reaction conditions. The only wholly satisfactory sulfating agent was found to be a complex of chlorosulfonic acid with aliphatic ethers such as diethyl ether. These complexes are formed by admixing the two components in molar ratios ranging from 0.5 to 4.0 moles of the ether for each mole of acid. The sulfation of the dioxolane is carried out at atmospheric or near atmospheric pressures between $-25°$ to $+35°$ C. preferably between $-10°$ to $+25°$ C. The molar ratio of sulfating complex to dioxolane varies between at least equimolar amounts, preferably to a slight excess (1.1–1.5:1) of sulfating complex to dioxolane.

To prepare the ammonium slat of the sulfated dioxolanes, the dioxolane is treated with at least a stoichiometric quantity of gaseous ammonia either neat or in the presence of inert solvent such as benzene or diethyl ether at temperatures ranging from $-25°$ C. to $+30°$ C.

The sodium and potassium salts are prepared in the usual fashion by contacting the sulfated dioxolane with aqueous solutions of the alkali metal hydroxide, carbonate or alkoxide.

C. Utilization of the Solubilized Dioxolanes as Surfactants.

1. Concentration. The sulfate, phosphate or alkoxylate containing dioxolane derivatives exhibit surfactant properties in aqueous solution in concentrations ranging from 0.01 weight percent and upwards. The upper limit is determined primarily by cost and for all but special purposes seldom exceeds 20% by weight. In all instances this concentration is referred to as a "surfactant amount" or "effective quantity of surfactant."

D. Utilization of the Solubilized Dioxolanes as Detergents

When the dioxolane derivatives are employed as detergents they ordinarily are present in at least the minimal concentrations disclosed supra accompanied by one or more of the following classes of materials which are generically referred to as detergent adjuvants:

1. Inorganic salts, acids and bases.

These are usually referred to as "builders." These salts usually comprise alkalies, phosphates and silicates of the alkali metals as well as their neutral soluble salts. These materials constitute from about 40 to 80 weight percent of the composition in which they are employed.

2. Organic builders or additives

These are substances which contribute to characteristics such as detergency, foaming power, emulsifying power or soil-suspending effect. Typical organic builders include sodium carboxymethyl cellulose, sequestering agents such as ethylenediaminetetraacetic acid and the fatty monoethanolamides, etc.

3. Special purpose additives

These include solubilizing additives such as lower alcohols, glycols and glycol ethers, bleaches or brighteners of various structures which share in common that they are dyestuffs and they do not absorb or reflect light in the visible range of the spectrum.

E. Testing and Evaluation Procedures

In order to accurately gauge the value of the solubilized dioxolanes as wetting, detergent and surfactant agents, carefully standardized procedures must be used. These are shown below:

1. Standard Launder-Ometer Test

Ten standard wash solutions ranging in detergent content from 0.05 to 0.30 weight percent (they are 0.015, 0.10, 0.10, 0.010, 0.20, 0.20, 0,30, 0.30) and ten standard wash solutions ranging in sodium sulfate content from 0.075 to 0.70 weight percent (they are 0.75, 0.067, 0.15, 0,133, 0.30, 0.466, 0.20, 0.45, 0.70) are prepared in 3,000 ppm hard water. The hard water was previously prepared by dissolving 26.43 grams of $CaCl_2.2H_2O$ in 600 ml of distilled water and mixing this solution with a solution of 29.58 grams of $MgSO_4.7H_2O$ in 600 ml of distilled water and making up the admixed solutions up to 10 liters with distilled water.

Standard soiled cloths containing the same amount of soil are placed in each solution and washed in a Launder-Ometer* for 10 minutes at 60° C. The cloths are removed from the wash solutions, rinsed, dried and the degree of whiteness measured by a Photovolt Reflectometer**. The data obtained are plotted and expressed as "Average Detergency Coefficient". This term is derived by expressing the soil removal properties of the experimental detergent as a percentage of a known standard detergent at 0.25 weight percent concentration.

*The apparatus used is designated Model B—5, Type LHD-HT by its distributor, Atlas Electric Devices Co. Chicago 13, Ill.
**Photovolt Reflectometer — The apparatus used is the Photovolt Reflection Meter 670, Search Unit 610—W sold by Photovolt Corporation, New York City, N.Y.

2. Standard Foam Test — This is the procedure described in ASTM procedure No. D1173-53.

EMBODIMENT A.

Preparation of
2,2-Dialkyl-4-Hydroxymethyl-1,3-Dioxolane.

To a reaction vessel equipped with heating, cooling and stirring means and means of stripping of a water azeotrope, is added 137 parts by weight of glycerol, 5 parts by weight of p-toluenesulfonic acid, 500 parts by weight of benzene and 260 parts by weight of a mixture $C_{10}-C_{15}$ aliphatic ketones having an average molecular weight of 185. The reaction mixture is stirred and refluxed for 65 hours while taking off the water toluene azeotrope. When water formation ceases the catalyst is removed by water washing and the solvent is distilled off. A product which I.R. and molecular weight analysis confirms to be the desired 2,2-dialkyl-4-hydroxymethyl-1,3-dioxolane is removed by vacuum distillation from unreacted ketone and higher molecular weight by-products. The dioxolane mixture had an average molecular weight of about 260.

Embodiments B to D:

Preparation of Specific Dioxolanes

Using the preparative procedure described by Berger, F.M., in Arch Intern Pharmacodyn, the following known 2,2-dialkyl-4-hydroxymethyl-(or methylol)-1,3-dioxolanes are prepared by condensing the indicated ketones with glycerol.

| | Aliphatic Ketone | Product |
|---|---|---|
| Embodiment B | diisopropyl | 2,2-diisopropyl-4 hydroxymethyl-1,3-dioxolane |
| Embodiment C | heptyl-methyl | 2,-methyl 2-heptyl-4 hydroxymethyl-1,3-dioxolane |
| Embodiment D | methyl-nonyl | 2-methyl-2-nonyl-4 hydroxymethyl-1,3-dioxolane |

Infra-red and molecular weight analysis confirms that the desired dioxolanes are prepared.

EXAMPLE 1.

Preparation of the Ethoxylate of 2,2-Dialkyl-4-Hydroxymethyl-1,3-Dioxolane

To an appropriate reaction flask equipped with a means of stirring, heating, cooling and passing gas into the flask, is added 50 parts by weight of 2,2-dialkyl-4-hydroxymethyl-1,3-dioxolane (having an average molecular weight of 260 whose preparation is described in Embodiment A) and 2 parts by weight of potassium hydroxide. Ethylene oxide is introduced into the flask at atmospheric pressure at a flow rate of 0.25 g. per minute while maintaining the temperature between 100° and 130° C. After 3 hours, 1 mole of ethylene oxide is added which amounts to about 5.3 moles of ethylene oxide/mole on the dioxolane. The addition of ethylene oxide is discontinued at this time, the solution is cooled to room temperature and 2.5 parts of concentrated (specific gravity 1.19) hydrochloric acid is added to the stirred reaction mixture. At this time the reaction mixture is filtered to remove insoluble matter and analysis shows the filtrate contains dioxolane ethoxylated with 5.2 moles of ethylene oxide.

EXAMPLE 2.

Preparation of a More Highly Ethoxylated Dioxolane.

Using the same reaction set-up, dioxolane and technique as described in Example 1, a 50 parts by weight portion of the dioxolane containing 1 part by weight of sodium metal catalyst is treated with 9.2 moles of ethylene oxide/mole is dioxolane over a 4 hour period at a reaction temperature between 95°–125° C. After acidification, cooling and filtration the product analyzed by molecular weight and hydroxyl number is found to be a 9.1 molar ethoxylate of 2,2-dialkyl-4-hydroxymethyl-1,3-dioxolane. This compound is a light yellow, free-flowing liquid that dissolves immediately in cold water.

By contrast, a 9-molar ethoxylate prepared in an identical manner from the condensation product of lauryl aldehyde and glycerol disclosed in Example 1 of British Pat. No. 414,772 is a viscous dark brown liquid, soluble in cold water only with difficulty. In the color test described in ASTM D 1500, the color of the ethoxylated dioxolane of Example 2 is found to be 0.05 wherein the ethoxylated acetal of British Pat. No. 414,772 is found to be 6.0.

EXAMPLE 3.

Preparation of Sulfated 2,2-Dialkyl-4-Methylol-1,3-Dioxolane.

A 50 parts by weight portion of the dioxolane prepared in Example A is admixed at −10° C. with a 58 parts by weight portion of 1:1 molar complex of chlorosulfonic acid with diethyl ether, previously prepared, and 50 parts by weight of diethyl ether in an appropriate reaction vessel having provisions for stirring, heating and cooling. After a period of 1 hour, the sulfation reaction is stopped and the product treated at −10° C. with an excess of $NH_3$ gas. Inorganic material is removed by filtration to obtain a good yield of the ammonium salt of sulfated dioxolane derivative, identified by I.R. and elemental analyses. This product exhibits desirable foaming properties (high but unstable foam, see Table II) in aqueous solution.

EXAMPLE 4.

Preparation of Phosphorylated Ketal.

A 26 parts by weight portion of the $C_{10}$—$C_{15}$ dioxolane prepared in Embodiment A is treated at 0° C. with 15 parts $POCl_3$ added over a 1 hour period. The mixture is stirred for 1 hour and added to an aqueous solution of 1.2 parts sodium hydroxide in a minimum amount of water at 0° C. The reaction mixture is then treated with a drying agent such as anhydrous $Na_2SO_4$ and is filtered to obtain the sodium salt of a phosphated dioxolane derivative.

EXAMPLE 5.

Evaluation of Illustrative Solubilized Dioxolanes as Surfactants and Comparisons of the Solubilized Surfactants with comparable commercially available products.

Testing Procedure - 2 methods of evaluation are used. They are entitled ASTM No. D1173-53 and Standard Launder-Ometer test.

The following tables summarize the properties of the products of Examples 1, 2 and 3 compared to comparable commercially utilized surfactants.

TABLE I

| Experimental Detergent | Average Detergency Coefficients (ADC) | ADC |
|---|---|---|
| Product from Example 1 | Commerical $C_{11}$–$C_{15}$ sec. alcohol 9-molar ethoxylate | 107 |
| Product from Example 2 | Commercial $C_{12}$–$C_{15}$ prim. alcohol 11-molar ethoxylate | 108 |
| Product from Example 3 | $NH_4^+$ salt of sulfated commercial $C_{11}$–$C_{15}$ sec. alcohol 3-molar ethoxylate | 105 |

TABLE II

| Detergent (at 1% concentration) | ASTM No. D1173-53 Foam Test Foam Height in mm. at | | | |
|---|---|---|---|---|
| | 0 | 5 | 10 | 15 min. |
| Product from Example 3 | 185 | 25 | 20 | 5 |
| NH$_4$+ salt of sulfated commercial C$_{11}$-C$_{15}$ sec. alcohol 3-molar ethoxylate | 200 | 190 | 165 | 155 |

EXAMPLES 6-8

Preparation of Ethoxylated Specific 2,2-Dialkyl-4-Methylol-1,3-Dioxolanes.

Using the procedure described in Example 1, 50 parts by weight portions of the specific dioxolanes, whose preparation is described in Embodiments B to D are ethoxylated by passing in an excess of ethylene oxide in the presence of potassium hydroxide, keeping the temperature between 100°–130° C. under a nitrogen atmosphere. After the desired extent of ethoxylation is achieved, the addition is discontinued and the catalyst is neutralized with concentrated hydrochloric acid, filtered and analysed as described in Example 1. The products with the degree of ethoxylation are given below:

| Dioxolane Product | Degree of Ethoxylation |
|---|---|
| 2,2-diisopropyl-4-hydroxymethyl-1,3-dioxolane | 12.5 molar |
| 2-methyl-2-heptyl-4-hydroxymethyl-1,3-dioxolane | 18.4 molar |
| 2-n-nonyl-2-methyl-4-hydroxymethyl-1,3-dioxolane | 15.4 molar |

In all instances good detergency coefficients are obtained using the previously described tests.

EXAMPLES 9-11

Preparation of Specific 2,2-Dialkyl-4-Methylol-1,3-Dioxolane Sulfates.

Using the sulfation procedure described in Example 3, 50 parts by weight portions of the specific dioxolanes whose preparation is described in Embodiments B to D, are sulfated using a stoichiometric excess of a chlorosulfonic diethyl ether complex (1:1 molar ratio) to dioxolane. The stirred mixture of sulfating agent, dioxolane and diethyl ether is kept at −10° C. for 1 hour in each instance. At this time the reaction is stopped and the isolation and purification procedure used in Example 3 is followed. The product's identity is confirmed by I.R. and elemental analysis. The products are the monosulfate of the named dioxolane in the "4" position.

EXAMPLE 9 2,2-disopropy-4-methylol-1,3-dioxolane 10 2-methyl, 2-heptyl-4-methylol-1,3-dioxolane 11 2-n-nonyl-2-methyl-4-methylol-1,3-dioxolane In all instances the monosulfates exhibited good detergency coefficients using the previously described standard test.

As the several embodiments and examples indicate, the novel invention is advantageous and gives rise to unexpected results in both its composition and process aspects. For example, the novel solubilized dioxolanes of this invention are superior surfactants in an aqueous environment. This has been demonstrated by their equivalent to slightly superior detergency when compared to the best comparable ethoxylated fatty alcohol commercial detergents. In addition, the solubilized surfactants are inexpensive, free flowing liquids that exhibit effective surfactant properties at relatively low concentrations. The finding that the solubilized ketals of this invention (formed from glycerol and aliphatic ketones containing 6 and higher carbon atoms) have substantially better solubility and color properties than the comparable solubilized acetals was particularly surprising.

Heretofore, based upon the disclosure of British Pat. No. 414,772 it would have been expected that the solubilized acetals (such as the alkoxylated condensation product of lauryl aldehyde and glycerol disclosed in Example 1 of the above patent) would have comparable properties to the seemingly related ketals. As Example 2 of this application indicates, this is not the case. For example, the solubilized ketals of this invention have substantially superior water solubility compared to the corresponding acetals of the British patent. In addition, the solubilized ketals of this invention are much lighter than the solubilized acetals. Inasmuch as the solubilized acetals of the British patent are structurally similar to the solubilized ketals, the substantial differences in color and solubility could scarcely be predicted.

The novel process of sulfating the dioxolanes (ketals) is also quite unexpected in view of the prior art. According to the same British patent one would expect that the sulfated ketals of this invention could be made as disclosed in the British patent simply from chlorosulfonating the ketal. However, surprisingly, the ketals of this invention are decomposed by sulfation with chlorosulfonic acid or sulfur trioxide-pyridine and can only be sulfonated in good yield using dialkyl ether - chlorosulfonic acid complexes. Example 3 of this application establishes this.

In view of the preceding specification it is apparent that numerous changes, modifications and substitutions can be made in choice of polyol or ketone reactant, solubilizing group and reaction conditions. The metes and bounds of this invention are best established by the claims which follow, read in the light of the specification.

What is claimed is:

1. Solubilized drivatives of 2,2-dialkyl-1,3-dioxolane-, 4 methylol included within the structure

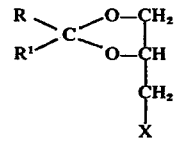

of which R—C—R' is the residuum of aliphatic ketones

wherein R and R' are alkyl groups which contain a total of 6 to 30 carbon atoms and X is a solubilizing group selected from alkoxylates containing 2 to 4 carbon atoms, sulfates and phosphates.

2. The solubilized derivatives of claim 1 wherein the aliphatic ketones comprise a mixture of different ketones containing 10 to 15 carbon atoms.

3. The solubilized derivatives of claim 2 wherein the solubilizing group is ethoxylate.

4. The solubilized derivatives of claim 2 wherein the solubilizing group is sulfate.

5. The solubilizing derivative of claim 3 containing from 1 to 20 moles of Ethoxylate.

6. A process for sulfating the dioxolane condensates of glycerol and aliphatic ketones wherein the aliphatic groups of the ketones total at least 6 carbon atoms, comprising contacting a dialkyl ether-chlorosulfonic acid complex containing at least a stoichiometric quantity of chlorosulfonic acid with said condensates at 25° C. to +30° C. until at least one sulfate group is added to said condensates.

7. The process of claim 6 wherein the aliphatic ketones comprise a mixture of aliphatic ketones containing from 10 to 15 carbon atoms.

8. The process of claim 6 wherein the molar ratio of dialkyl ether to chlorosulfonic acid varies from 0.5 to 4.0 moles of the ether for each mole of acid.

9. The sulfated dioxolane condensates of claim 6.

10. Salts of sulfated 2,2-dialkyl-4-hydroxymethyl-1,3-dioxolane, wherein the cation is selected from the group consisting of ammonium and the alkali metals.

11. The ammonium salt of 2,2-dialkyl-4-hydroxymethyl-1,3-dioxolane.

* * * * *